United States Patent
Cekic et al.

(10) Patent No.: US 6,649,921 B1
(45) Date of Patent: Nov. 18, 2003

(54) APPARATUS AND METHOD PROVIDING SUBSTANTIALLY TWO-DIMENSIONALLY UNIFORM IRRADIATION

(75) Inventors: Miodrag Cekic, Bethesda, MD (US); Boris Geller, Germantown, MD (US)

(73) Assignee: Fusion UV Systems, Inc., Gaithersburg, MD (US)

( * ) Notice: Subject to any disclaimer, the term of this patent is extended or adjusted under 35 U.S.C. 154(b) by 0 days.

(21) Appl. No.: 10/222,995

(22) Filed: Aug. 19, 2002

(51) Int. Cl.[7] .................... G21F 5/02; A61N 5/00; G01N 21/00; G02B 1/12; G21H 5/00
(52) U.S. Cl. .................. 250/504 R; 250/491.1; 250/492.2; 250/492.3; 250/493.1; 250/496.1; 250/498.1; 250/519.1
(58) Field of Search .................. 250/504 R, 491.1, 250/492.2, 492.3, 493.1, 496.1, 498.1, 519.1

(56) References Cited

U.S. PATENT DOCUMENTS

| | | | |
|---|---|---|---|
| 4,010,374 A | | 3/1977 | Ramler |
| 4,019,062 A | * | 4/1977 | Rongren .................. 250/492.1 |
| 4,048,490 A | | 9/1977 | Troue |
| 4,276,479 A | | 6/1981 | Mibu et al. |
| 4,287,554 A | * | 9/1981 | Wolff ...................... 362/218 |
| 4,297,583 A | | 10/1981 | Nerod |
| 4,348,105 A | | 9/1982 | Caprari |
| 4,503,086 A | | 3/1985 | Schultz |
| 4,560,883 A | * | 12/1985 | Kerschgens ............. 250/504 R |
| 4,569,003 A | * | 2/1986 | Elmer et al. ................ 362/147 |
| 4,726,949 A | | 2/1988 | Miripol et al. |
| 4,812,957 A | | 3/1989 | Hill |
| 4,839,513 A | * | 6/1989 | Wijtsma .................. 607/94 |
| 4,880,988 A | * | 11/1989 | Witt ........................ 250/504 R |
| 4,897,771 A | * | 1/1990 | Parker ...................... 362/298 |
| 5,029,252 A | * | 7/1991 | Ameseder ............... 250/455.11 |
| 5,130,553 A | | 7/1992 | Amoh |
| 5,176,782 A | | 1/1993 | Ishibashi et al. |
| 5,211,467 A | | 5/1993 | Seder |
| 5,269,867 A | | 12/1993 | Arai |
| 5,411,588 A | * | 5/1995 | Diepens et al. ............. 118/666 |
| 5,440,137 A | | 8/1995 | Sowers |
| 5,494,576 A | | 2/1996 | Hoppe et al. |
| 5,635,133 A | | 6/1997 | Glazman |
| 5,699,185 A | | 12/1997 | MacDonald et al. |
| 5,760,408 A | | 6/1998 | Kikuchi et al. |
| 5,817,276 A | | 10/1998 | Fencl et al. |
| 5,839,078 A | | 11/1998 | Jennings et al. |
| 5,898,809 A | | 4/1999 | Taboada et al. |
| 5,922,605 A | | 7/1999 | Feurstein et al. |
| 5,932,886 A | | 8/1999 | Arai et al. |
| 5,973,331 A | | 10/1999 | Stevens et al. |
| 5,989,283 A | * | 11/1999 | Wilkens ...................... 607/88 |
| 6,124,600 A | | 9/2000 | Moroishi et al. |
| 6,128,030 A | | 10/2000 | Kikuchi et al. |
| 6,190,016 B1 | | 2/2001 | Suzuki et al. |
| 6,333,509 B1 | * | 12/2001 | Lumpp ................... 250/504 R |
| 2002/0034012 A1 | * | 3/2002 | Santoro et al. ............. 359/599 |

* cited by examiner

Primary Examiner—John R. Lee
Assistant Examiner—Mary El-Shammaa
(74) Attorney, Agent, or Firm—Antonelli, Terry, Stout & Kraus, LLP (57) ABSTRACT

Apparatus and method providing substantially two-dimensionally uniform irradiation of a planar target surface. An irradiation source is within an elliptical reflecting trough, on the major axis of the trough, and spaced from the focal axes of the trough. Edges of the trough define a first plane substantially perpendicular to the major axis of the trough. Reflectors extend substantially equal distances from the longitudinal edges and the ends of the trough to define a target surface plane substantially parallel with the first plane. A translucent reflector is a positioned on the major axis of the trough, outside the trough. The translucent reflector has a first planar portion lying in a plane substantially parallel with the target surface plane, and second and third planar portions extending from the edges of the first planar portion and angled toward the target surface plane.

32 Claims, 6 Drawing Sheets

APPARATUS AND METHOD PROVIDING SUBSTANTIALLY TWO-DIMENSIONALLY UNIFORM IRRADIATION

FIELD OF THE INVENTION

The present invention pertains to an apparatus and method providing substantially two-dimensionally uniform irradiation of large areas with a high level of irradiation. More particularly, the present invention pertains to an apparatus for and a method of uniformly projecting a high level of irradiation onto a large planar target surface so as to uniformly treat the surface.

BACKGROUND OF THE INVENTION

Various manufacturing processes include treating a planar surface by irradiating the surface with, for example, ultraviolet light or other irradiation. The irradiation treatment may be related to curing, purification, disinfection, advanced oxidation or some other procedure. By way of example, manufacturing of printed circuit boards frequently involves forming conductive paths by a photoresist process in which a board treated with a photoresist in a desired pattern is irradiated as a part of a process to remove material from specified areas on the board. Similarly, in some printing processes a printed pattern is cured by irradiating the pattern. Obtaining a high quality, uniform product requires irradiating a two-dimensionally uniform high level of irradiation over the entire target area. Otherwise irregularities in the finished product may result.

Existing devices often expose the central area of the irradiated surface to more irradiation than the edge areas of the surface. The areas of high irradiation may receive more than the desired level, possibly causing damage, while the areas of low irradiation may be undertreated. This problem is even greater in the treating of relatively large planar surfaces when a relatively high level of irradiance is needed.

Various techniques have been used in the past to control the uniformity of irradiation of planar target surfaces. By way of example, U.S. Pat. No. 4,010,374 discloses an ultraviolet light processor including a primary light source which exposes a target surface on a work piece to ultraviolet light with the ultraviolet flux incident per unit area of the target surface greater at the central region of the surface than at edges of the surface, and a secondary light source which is positioned in a different plane than the primary light source and which exposes the target surface to ultraviolet light with the ultraviolet flux incident per unit area of the surface greater at the edge areas of the target surface than at the central region. Not only is such an ultraviolet light processor complex and expensive to manufacture and to operate, but also it is difficult to control in a manner that maintains the ultraviolet irradiation received at the edge areas of the target surface from the secondary source at substantially the same level as the ultraviolet irradiation received at the central area of the target surface from the primary source. In addition, the multiple irradiation sources often result in excessive heat which must be removed to avoid deformation, color change, or other damage to the irradiated surface.

U.S. Pat. No. 4,276,479 discloses a tunnel type irradiation chamber with a plurality of cylindrical ultraviolet lenses through which an object to be treated is conveyed. Two sets of irradiation sources, providing light of two different wavelengths, are within the chamber, providing light in two stages. Not only is this apparatus complex to control, but also it frequently does not provide uniform irradiation distribution on the object surface.

U.S. Pat. No. 4,348,015 shows an irradiation projection system including complex lenses in order to provide uniform irradiance. Numerous other systems have been attempted. These generally are complex and expensive, both to construct and to operate. Even so, they generally have difficulty in achieving uniform irradiance, particularly two-dimensionally uniform irradiance.

SUMMARY OF THE INVENTION

The present invention is an apparatus for and a method of providing substantially two-dimensionally uniform irradiation of planar areas with a high level of irradiation. In accordance with the present invention, an elongated source of irradiation, such as an elongated discharge tube, is arranged within an elongated elliptical reflecting trough, with the irradiation source spaced from the focal axis within the trough. The trough longitudinal edges define a first plane substantially perpendicular to the trough major axis. First and second reflectors extend from the trough longitudinal edges. Third and fourth reflectors extend from the ends of the trough. The first, second, third, and fourth reflectors extend to reflector outer edges which define the plane of the target surface. That target surface plane is substantially parallel with the first plane. Preferably, the first reflector includes a first portion extending from one longitudinal edge of the trough and angled toward the target surface at an angle greater than 0° with respect to the first plane, and a second portion extending from the first portion and angled toward the target surface at an angle greater than 90° with respect to the first plane. Similarly, the second reflector preferable includes a first portion extending from the other trough longitudinal edge and angled toward the target surface at an angle greater than 0° with respect to the first plane, and a second portion extending from the first portion and angled toward the target surface at an angle greater than 90° with respect to the first plane. Preferably, also, the first and second reflectors are cold reflectors.

An elongated central reflector is positioned on the trough major axis, outside the trough and has a first planar portion lying in a plane substantially parallel with the target surface plane. The first planar portion longitudinal axis extends substantially parallel with the longitudinal axis of the irradiation source. Preferably, the central reflector includes second and third planar portions extending from the longitudinal edges of the first planar portion. Each of the second and third planar portions is angled toward the target surface at an angle greater than 0° with respect to the plane of the first planar portion. Preferably, also, the central reflector is a translucent mirror.

In a preferred embodiment, the second portion of the first reflector has an ultraviolet light reflectance $\rho uv1$, the second portion of the second reflector has an ultraviolet light reflectance $\rho uv2$, the third reflector has an ultraviolet light reflectance $\rho uv3$, the fourth reflector has an ultraviolet light reflectance $\rho uv4$, the first portion of the first reflector has an ultraviolet light reflectance $\rho uv5$, the first portion of the second reflector has an ultraviolet light reflectance $\rho uv6$, the translucent reflector first planar portion has an ultraviolet light reflectance $\rho uv7$, the translucent reflector second planar portion has an ultraviolet light reflectance $\rho uv8$, and the translucent reflector third planar portion has an ultraviolet light reflectance $\rho uv9$, and $\rho uv1 = \rho uv2 = \rho uv3 = \rho uv4 > \rho uv5 = \rho uv6 > \rho uv7 > \rho uv8 = \rho uv9$. In a particularly preferred embodiment, $\rho uv1 = \rho uv2 = \rho uv3 = \rho uv4 = 100\%$; $\rho uv5 = \rho uv6 =$ 90%, ρuv7=65%, and ρuv8=ρuv9=60%, surface reflection losses not being included.

The source of irradiation can be a light source, preferably a source of ultraviolet light such a microwave electrodeless discharge tube, an arc discharge bulb, or a fluorescent discharge bulb, for example. If desired, the position of the discharge tube can be adjustable within the elliptical reflecting trough, aiding in optimization of the uniformity of the irradiation distribution on the planar target surface.

BRIEF DESCRIPTION OF THE DRAWINGS

These and other aspects and advantages of the present invention are more apparent from the following detailed description and claims, particularly when considered in conjunction with the accompanying drawings. In the drawings:

DETAILED DESCRIPTION OF PREFERRED EMBODIMENTS

In the following description of the present invention, reference is made to the accompanying drawings which form a part hereof and which show by way of illustration a preferred embodiment in which the invention may be practiced. It is to be understood that other embodiments may be utilized, and that structural and functional modifications may be made without departing from the scope of the present invention.

Figure 1:
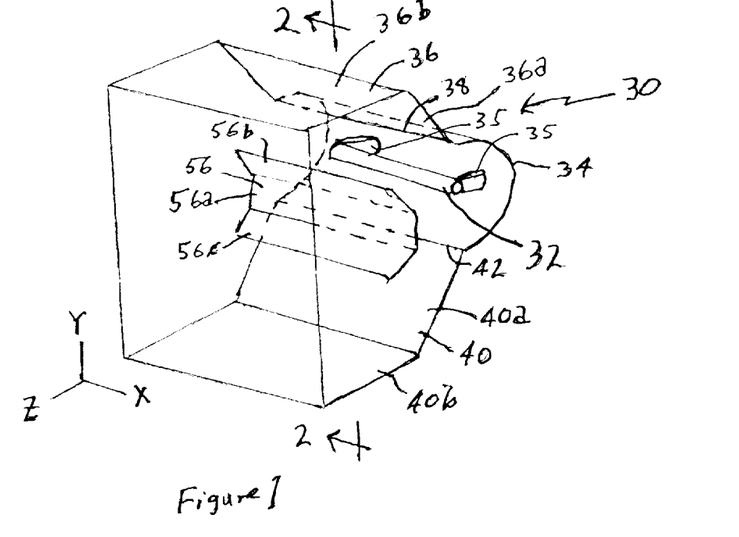
FIG. 1 is a perspective view of a preferred embodiment of an apparatus for providing substantially uniform irradiation of a planar target surface in accordance with the present invention.
Figure 2:
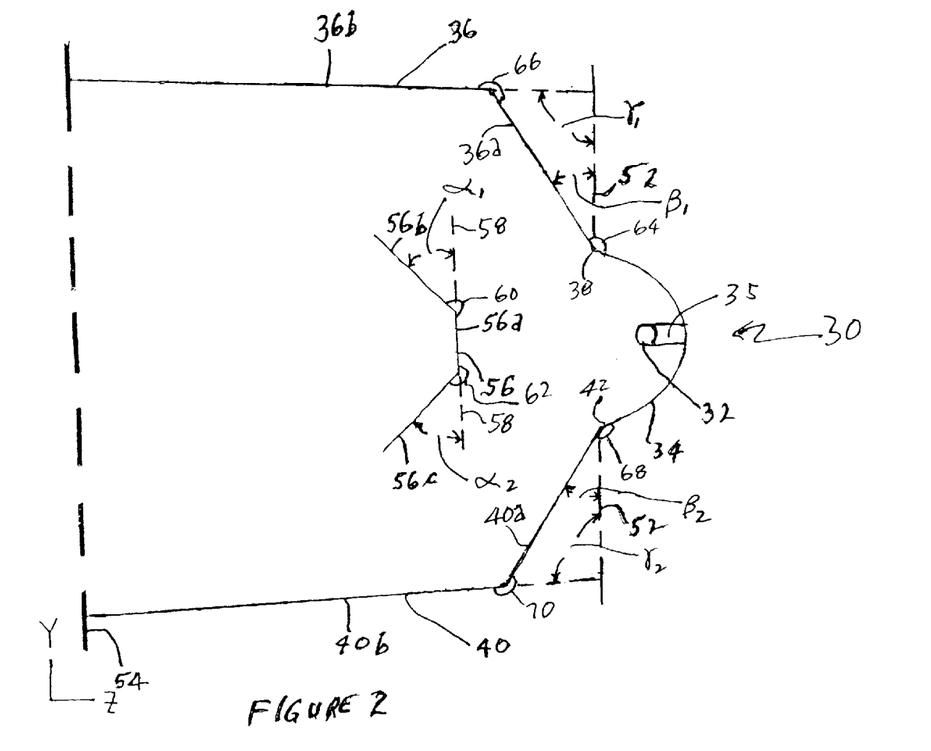
FIG. 2 is a sectional view taken along line 2—2 in FIG. 1.
Figure 3:
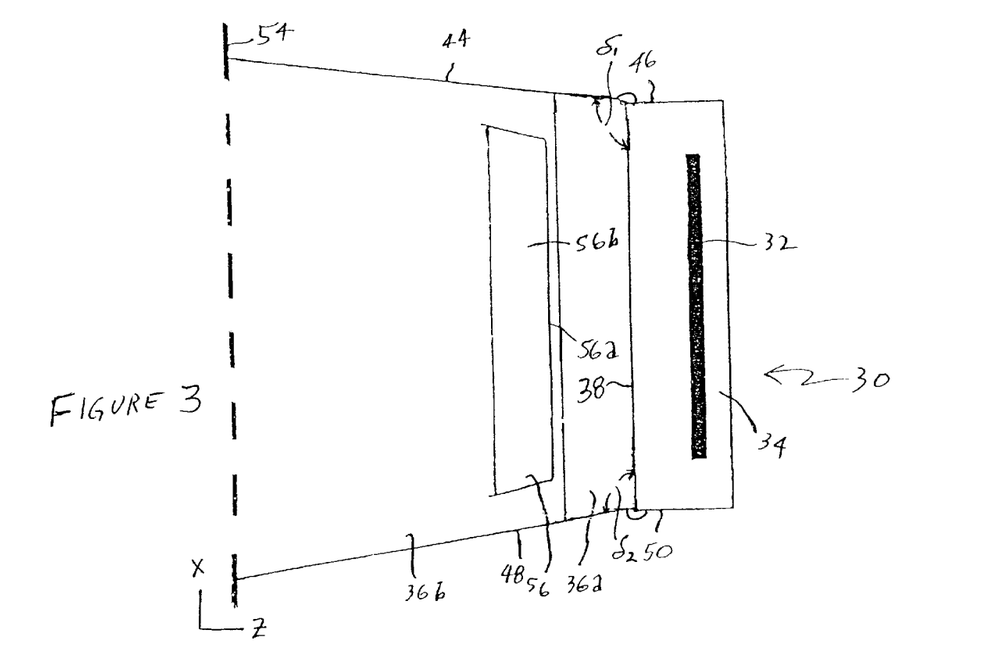
FIG. 3 is a top plan view of the apparatus of FIG. 1.

FIGS. 1–3 depict a preferred embodiment of an irradiation apparatus 30 in accordance with the present invention. Apparatus 30 includes an irradiation source 32, which is depicted as an elongated discharge bulb, for example a tubular bulb. Irradiation source 32 preferably is a light source such as source of ultraviolet light, and for example might be a microwave electrodeless discharge bulb, an arc discharge bulb, or a fluorescent discharge bulb. By way of example, in a low power irradiation apparatus in accordance with the present invention, irradiation source 32 might be a six-inch long, 2400 watt ultraviolet lamp, while than a higher power apparatus, source 32 might be a ten inch long, six kilowatt ultraviolet lamp. Irradiation source 32 is positioned within an elongated elliptical reflecting trough 34, which preferably is substantially one-half of an ellipse, although the reflecting trough could be less than one-half an ellipse if desired. Since it is part of an ellipse, reflecting trough 34 has a major axis, a minor axis, a first focal axis within the trough, and a second focal axis outside the trough. Irradiation source 32 is positioned on the major axis of trough 34, spaced from the first focal axis. Adjustable connectors 35; might be provided to movably mount irradiation source 32 within elliptical reflecting trough 34, permitting adjustment of the position of the irradiation source relative to the first focal axis of the trough. Irradiation source 32 has a longitudinal axis substantially parallel with the first focal axis of trough 34.

A first reflector 36 extends from a first longitudinal edge 38 of trough 34, while a second reflector 40 extends from second longitudinal edge 42. A third reflector 44 extends from first end 46 of trough 34, and a fourth reflector 48 extends from second end 50 of the trough.

Longitudinal edges 38 and 42 of trough 34 define a first plane 52 which is substantially perpendicular to the major axis of trough 34. Reflectors 36, 40, 44, and 48 extend substantially equal distances from trough 34 to reflector outer edges which define a target plane 54 substantially parallel with plane 52.

A translucent reflector 56 is positioned on the major axis of trough 34, beyond edges 38 and 42 and so outside the trough. Reflector 56 includes a first planar reflector portion 56a lying in a plane 58 which is substantially parallel with planes 52 and 54. First planar reflector portion 56a is substantially the same length as irradiation source 32 and has a longitudinal axis extending substantially parallel with the longitudinal axis of irradiation source 32.

Preferably, translucent reflector 56 further includes a second planar reflector portion 56b, which is pivotally connected to a first longitudinal edge of first planar reflector portion 56a by a pivotal connector 60, and a third planar reflector portion 56c, which is connected to the second longitudinal edge of first planar reflector portion 56a by a pivotal connector 62. Second and third planar portion are angled toward target surface plane 54 at angles $\alpha_1 > 0°$ and $\alpha_2 > 0°$ with respect to plane 58. Preferably, $a_1 = \alpha_2$ and typically might be in the order of $X^O$.

In a preferred embodiment, first reflector 36 includes a first portion 36a and a second portion 36b. First portion 36a of first reflector 36 is pivotally attached to first longitudinal edge 38 of trough 34 by a pivotal connector 64, while second portion 36b of first reflector 36 is pivotally connected to first portion 36a of first reflector 36 by another pivotal connector 66. Similarly, second reflector 40 includes a first portion 40a and a second portion 40b. First portion 40a of second reflector 40 is pivotally connected to second longitudinal edge 42 of trough 34 by a pivotal connector 68, while second portion 40b of second reflector 40 is pivotally connected to first portion 40a of second reflector 40 by a pivotal connector 70. First portions 36a and 40a of first and second reflectors 36 and 40 are angled toward target surface plane 54 at angles $\beta_1 > 0°$ and $\beta_2 > 0°$, while second portions 36b and 40b of first and second reflectors 36 and 40 are angled toward target surface plane 54 at angles $\gamma_1 > 90°$ and $\gamma_2 > 90°$ with respect to plane 52. Preferably $\beta_1 = \beta_2$ and typically might be in the order of 30° and $\gamma_1=\beta_2$ and typically might be in the order of 105°.

In a similar manner, third reflector 44 and fourth reflector 48 are connected to first and second ends 46 and 50 of trough 34 by pivotal connectors 72 and 74, respectively, and are angled toward target plane 54 at angles $\delta_1>90°$ and $\delta_2>90°$ with respect to first and second longitudinal edges 38 and 42 of the trough, which define first plane 52. Preferably, $\delta_1=\delta_2$ and typically might be in the order of 105°.

Preferably reflectors 36, 40, 44, and 48 are dichroic reflectors. More preferably, reflectors 36, 40, 44, and 48 are cold reflectors which reflect ultraviolet irradiation and a part of visible light while transmitting infrared irradiation and a part of visible light.

In a preferred embodiment, second portion 36b of first reflector 36 has an ultraviolet light reflectance $\rho uv1$, second portion 40b of second reflector 40 has an ultraviolet light reflectance $\rho uv2$, third reflector 44 has an ultraviolet light reflectance $\rho uv3$, fourth reflector 48 has an ultraviolet light reflectance $\rho uv4$, first portion 36a of first reflector 36 has an ultraviolet light reflectance $\rho uv5$, first portion 40a of second reflector 40 has an ultraviolet light reflectance $\rho uv6$, first planar portion 56b of translucent reflector 56 has an ultraviolet light reflectance $\rho uv7$, second planar portion 56b of translucent reflector 56 has an ultraviolet light reflectance $\rho uv8$, and third planar portion 56c of translucent reflector 56 has an ultraviolet light reflectance $\rho uv9$, and $\rho uv1=\rho uv2=\rho uv3=\rho uv4>\rho uv5=\rho uv6>\rho uv7>\rho uv8=\rho uv9$. In a particularly preferred embodiment, $\rho uv1=\rho uv2=\rho uv_3=\rho uv4=100\%$, $\rho uv5=\rho uv6=90\%$, $\rho uv7=65\%$, and $\rho uv8=\rho uv9=60\%$, surface reflecting losses not being included.

Figure 4:
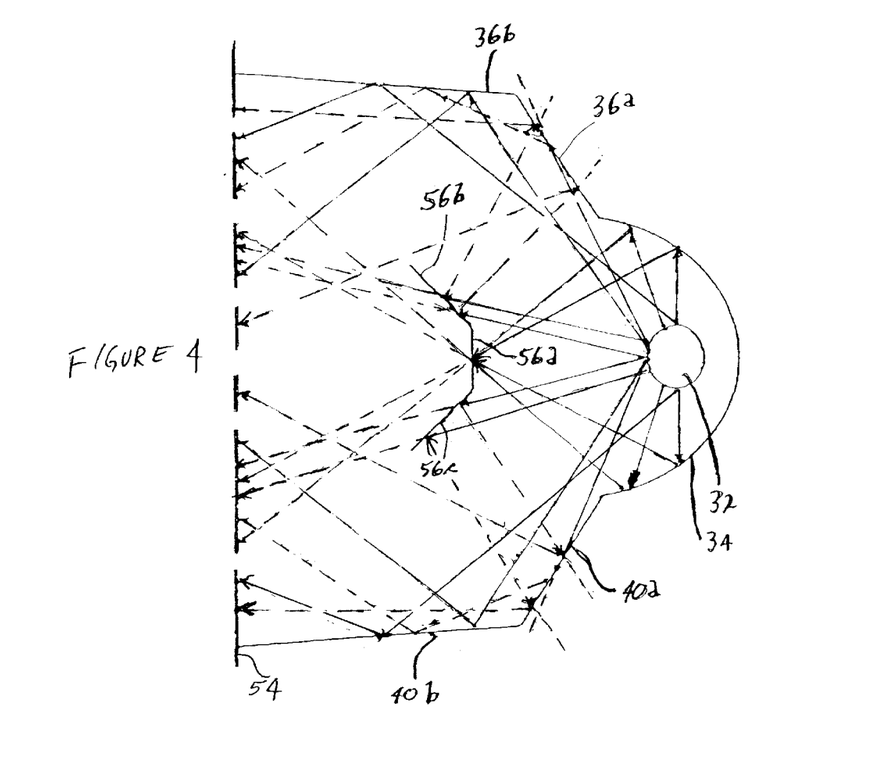
FIG. 4 is a schematic view illustrating typical optical paths within the apparatus of FIG. 1, based on a computer simulation.

FIG. 4 is a schematic view of apparatus 30 illustrating typical irradiation paths within the apparatus; based on a computer simulation. FIG. 4, of course, does not show all of the irradiation paths, but only illustrates typical paths. As can be seen, translucent reflector 56 results in the irradiation from source 32 reaching target plane 54 with a substantially uniform irradiation distribution.

To optimize the uniformity of the irradiation distribution on target surface plane 54, second and third planar portions 56b and 56c of translucent reflector 56 can be pivoted as necessary. In addition, further optimization of the irradiation uniformity can be achieved by pivoting of first and second portions 36a, 36b, 40a, and 40b of first and second reflectors 36 and 40, as well as by pivoting of reflectors 44 and 48. Additionally, these reflectors might be pivoted to accommodate targets of different sizes on plane 54. The edges of reflectors 36, 40, 44, and 48 may be joined by flexible, or telescoping reflective material, if desired, to accommodate such pivoting.

To show the advantages of the present invention, the following examples were obtained using computer simulations.

Figure 5:
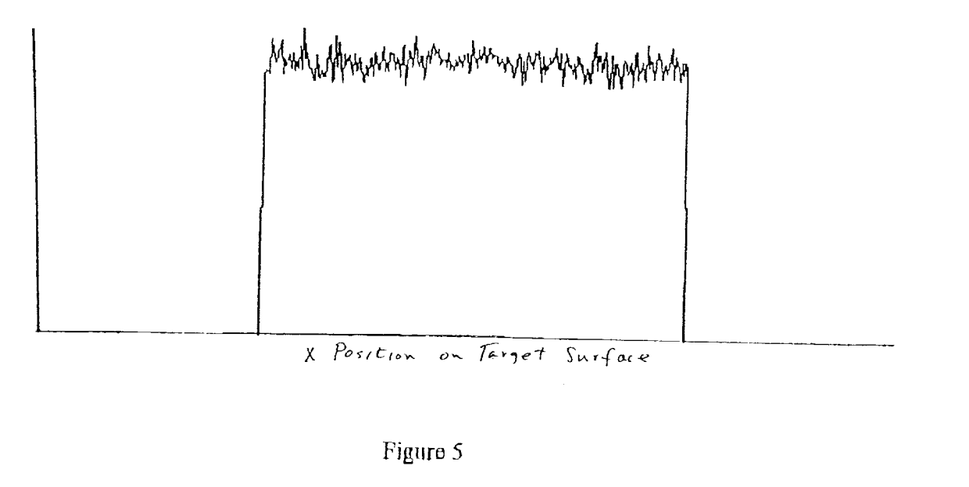
FIGS. 5 and 6 illustrate the irradiation distribution on a planar target surface irradiated by an apparatus in accordance with FIG. 1, based on a computer simulation.
Figure 6:
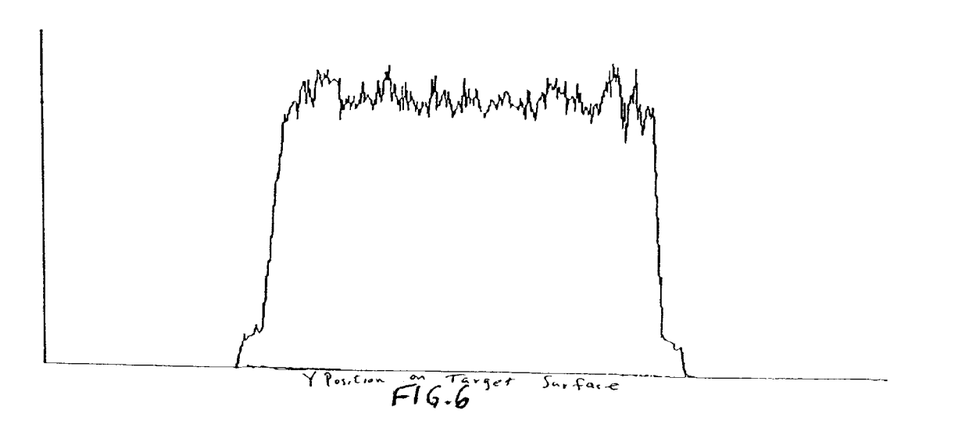
Figure 7:
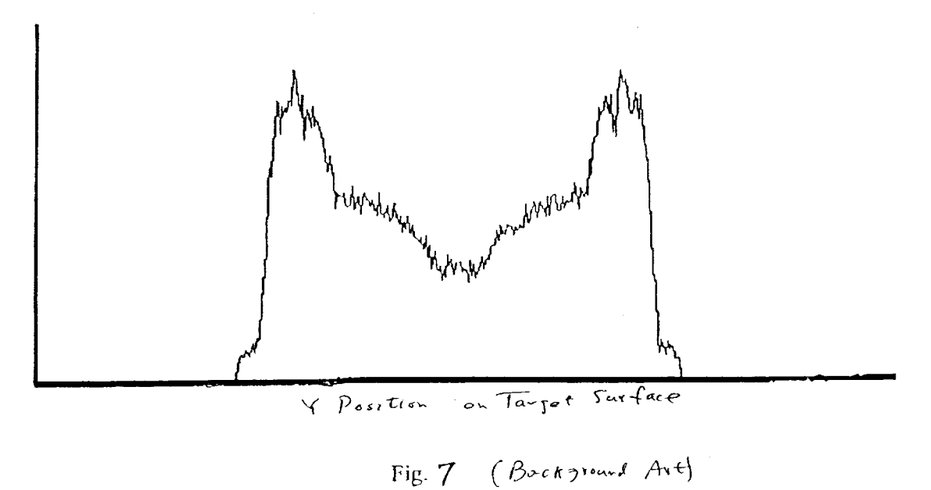
FIG. 7 illustrates the irradiation distribution of an apparatus having reflecting surfaces within 100% reflectance, based on a computer simulation, surface reflection losses not being included.
Figure 8:
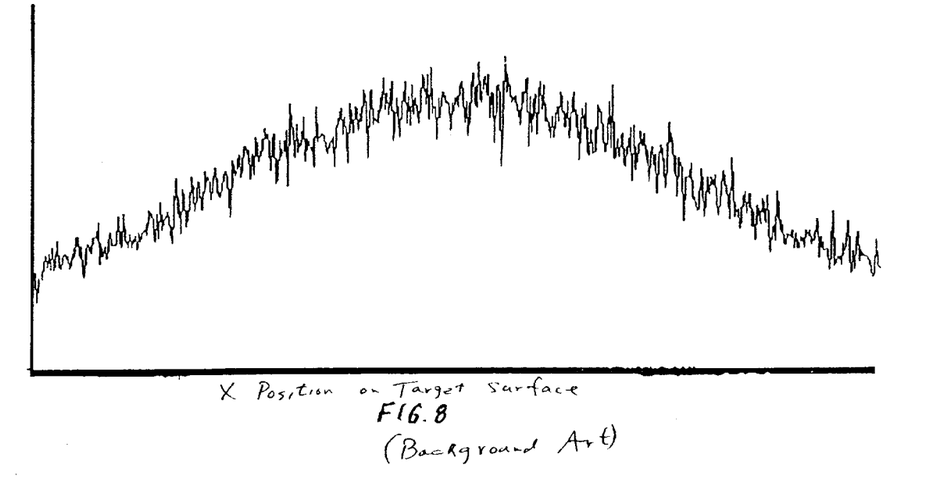
FIG. 8 illustrates the irradiation distribution of an apparatus omitting certain reflectors, based on a computer simulation.

FIGS. 5 and 6 illustrate the X dimension and Y dimension irradiation distribution on target surface 54 using apparatus 30, based on a computer simulation. The X and Y axes are shown in FIGS. 1–3. Irradiation source 32 is a ten inch, six-kilowatt ultraviolet electrodeless discharge tube. Trough 34 is one-half of an ellipse having a major axis of approximately six inches and a minor axis of approximately 4¼ inches. Irradiation source 32 is positioned on the major axis of trough 34 at the location found to provide optimum achievable uniformity of the irradiation distribution on target surface 38. Translucent reflector 56 is at the second focal axis of elliptical trough 34. Target surface 38 is a 24 inch by 24 inch photosensitive film positioned 24 inches from trough 34. Angles $\alpha_1$ and $\alpha_2=45°$; angles $\beta_1$ and $\beta_2=30°$; angles $\gamma_1$ and $\gamma_2=105°$; and angles $\delta_1$ and $\delta_2=105°$. As can be seen, the irradiation distribution is substantially uniform over the full target area. In contrast, FIG. 7 illustrates the Y direction irradiation distribution in a similar apparatus but having an ultraviolet light reflectance of 100% for all of the reflectors 36, 40, 44, and 48. In further contrast, FIG. 8 illustrates the X direction irradiation distribution for an apparatus similar to apparatus 30, but omitting reflectors 44 and 48.

Figure 9:
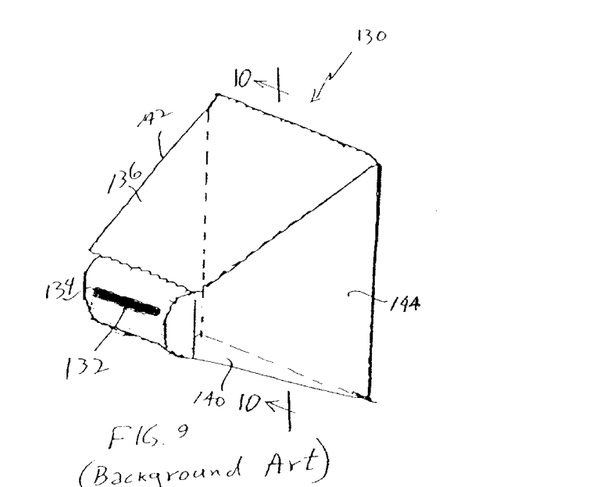
FIG. 9 is a rear perspective view of a known apparatus for irradiating a planar target surface.
Figure 10:
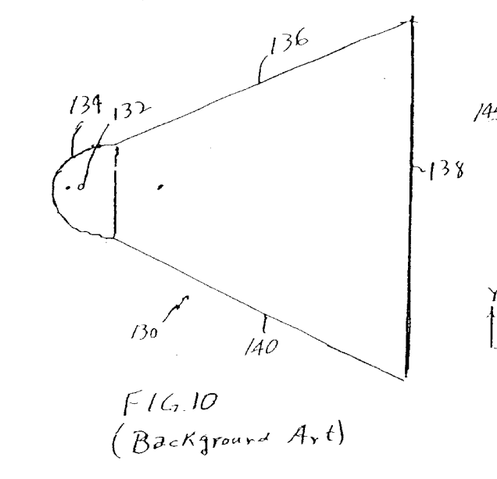
FIG. 10 is a sectional view taken along line 10—10 in FIG. 9.
Figure 11:
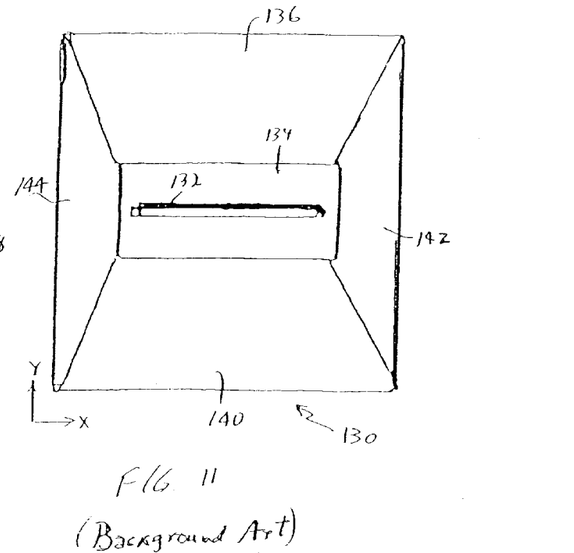
FIG. 11 is a front elevation view of the apparatus of FIG. 9.

As a further comparison, FIGS. 9, 10, and 11 depict an apparatus 130 omitting translucent mirror 56. FIGS. 9–11 are respectively a perspective view, a schematic sectional view, and a front elevational view of apparatus 130. Apparatus 130 includes an elongated irradiation source 132 positioned within an elongated elliptical reflecting trough 134. First and second reflectors 136 and 140 extend from longitudinal edges 138 and 142 of trough 134 to a target surface 138. Third and fourth reflectors 142 and 144 extend from the ends of trough 134 to target surface 138. Target surface 138 is a 24 inch×24 inch surface positioned 24 inches from trough 134.

Figure 12:
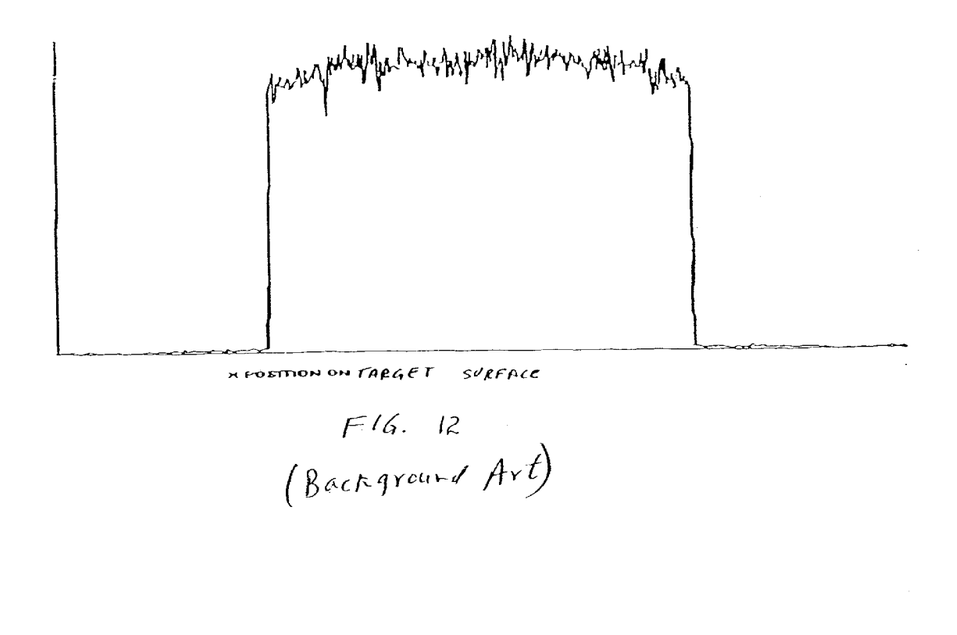
FIGS. 12 and 13 illustrate the irradiation distribution of the apparatus of FIGS. 9–11, based on a computer simulation.
Figure 13:
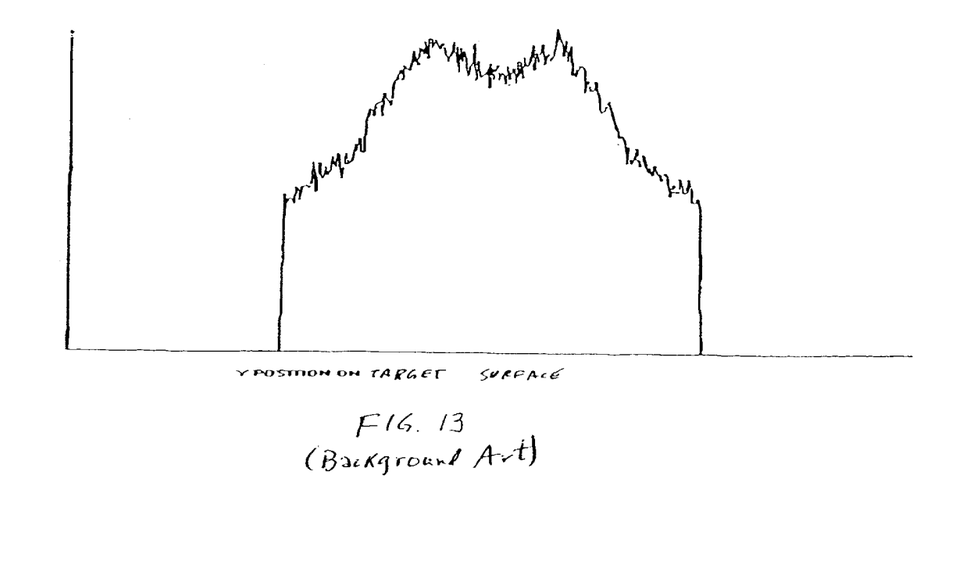

Irradiation source 132 is a ten inch, six-kilowatt ultraviolet electrodeless discharge tube. Trough 134 is one-half of an ellipse having a major axis of approximately six inches and a minor axis of approximately 4¼ inches. Irradiation source 132 is positioned on the major axis of trough 134 at the location found to provide optimum achievable uniformity of the irradiation distribution on target surface 138. FIG. 12 depicts the horizontal or X direction distribution of the irradiation reaching target surface 138, while FIG. 13 depicts the vertical or Y direction distribution. The X and Y directions are shown in FIG. 11. While the X direction distribution is somewhat uniform, the Y direction distribution is clearly non-uniform. Apparatus 30 of FIGS. 1–3 provides improved two-dimensional uniformity of irradiation distribution on a planar target surface as compared with apparatus 130.

The present invention thus presents an apparatus for and a method of providing substantially uniform irradiation of a relatively large target surface. Although the invention has been described with reference to a preferred embodiment, alternations, variations and substitutions could be made, and still the result would be within the scope of the invention.

What is claimed is:

1. Apparatus for providing substantially two-dimensionally uniform irradiation of a relatively large planar target surface, said apparatus comprising:

an elliptical reflecting trough having a major axis, a minor axis, a first focal axis within said trough and a second focal axis outside said trough, said trough terminating in an opening with longitudinal edges defining a first plane substantially perpendicular to the major axis of said trough, the first and second longitudinal edges extending between first and second ends of said trough;

a first reflector extending from the first longitudinal edge of said trough;

a second reflector extending from the second longitudinal edge of said trough;

a third reflector extending from the first end of said trough;

a fourth reflector extending from the second end of said trough;

an irradiation source for producing irradiation to irradiate the target surface, said irradiation source being within said trough, on the major axis of said trough, spaced from the first focal axis of said trough and having a longitudinal axis substantially parallel with the trough first focal axis; and a translucent reflector positioned on the major axis of said trough and outside said trough, said translucent reflector having a first planar portion lying in a plane substantially parallel with the target surface plane and having a longitudinal axis extending substantially parallel with the irradiation source longitudinal axis, wherein, said first, second, third, and fourth reflectors extend substantially equal distances from said trough to reflector outer edges to define a plane for the target surface substantially parallel with the first plane.

2. Apparatus as claimed in claim 1, wherein each of said first, second, third, and fourth reflectors comprises a dichroic mirror.

3. Apparatus as claimed in claim 2, wherein each of said first, second, third, and fourth reflectors comprises a cold mirror.

4. Apparatus as claimed in claim 1, wherein:

said translucent reflector first planar portion has first and second longitudinal edges; and said translucent reflector further includes a second planar portion extending from said first planar portion first longitudinal edge and angled toward the target surface plane at an angle $\alpha_1>0°$ with respect to the plane of said first planar portion, and a third planar portion extending from said first planar portion second longitudinal edge and angled toward the target surface plane at an angle $\alpha_2>0°$ with respect to the plane of said first planar portion.

5. Apparatus as claimed in claim 4, further comprising mounts pivotally mounting said translucent reflector second and third planar portions to the first and second longitudinal edges of said first planar portion, respectively, permitting adjustment of the angles $\alpha_1$ and $\alpha_2$.

6. Apparatus as claimed in claim 4, wherein $\alpha_1=\alpha_2$.

7. Apparatus as claimed in claim 4, wherein:

said first reflector includes a first portion extending from the first longitudinal edge of said trough and angled toward the target surface plane at an angle $\beta_1>0°$ with respect to the first plane, and a second portion extending from the first reflector first portion and angled toward the target surface at an angle $\gamma_1>90°$ with respect to the first plane; and said second reflector includes a first portion extending from the second longitudinal edge of said trough and angled toward the target surface plane at an angle $\beta_2>0°$ with respect to the first plane, and a second portion extending from the second reflector first portion and angled toward the target surface at an angle $\gamma_2>90°$ with respect to the first plane.

8. Apparatus as claimed in claim 7, wherein:

said second portion of said first reflector has a ultraviolet light reflectance $\rho uv1$, said second portion of said second reflector has a ultraviolet light reflectance $\rho uv2$, said third reflector has a ultraviolet light reflectance $\rho uv3$, said fourth reflector has a ultraviolet light reflectance $\rho uv4$, said first portion of said first reflector has a ultraviolet light reflectance $\rho uv5$, said first portion of said second reflector has a ultraviolet light reflectance $\rho uv6$, said translucent reflector first planar portion has a ultraviolet light reflectance $\rho uv7$, said translucent reflector second planar portion has a ultraviolet light reflectance $\rho uv8$, and said translucent reflector third planar portion has a ultraviolet light reflectance $\rho uv9$; and $\rho uv1=\rho uv2=\rho uv3=\rho uv4>\rho uv5=\rho uv6>\rho uv7>\rho uv8=\rho uv9$.

9. Apparatus as claimed in claim 1, wherein:

said first reflector includes a first portion extending from the first longitudinal edge of said elliptical trough and angled toward the target surface plane at an angle $\beta_1>0°$ with respect to the first plane, and a second portion extending from the first reflector first portion and angled toward the target surface at an angle $\gamma_1>90°$ with respect to the first plane; and said second reflector includes a first portion extending from the second longitudinal edge of said trough and angled toward the target surface plane at an angle $\beta_2>0°$ with respect to the first plane, and a second portion extending from the second reflector first portion and angled toward the target surface at an angle $\gamma_2>90°$ with respect to the first plane.

10. Apparatus as claimed in claim 9, further comprising mounts pivotally mounting said first reflector first portion and said second reflector first portion to the first and second longitudinal edges of said trough, respectively, permitting adjustment of the angles $\beta_1$ and $\beta_2$.

11. Apparatus as claimed in claim 10, further comprising further mounts pivotally mounting said first reflector second portion and said second reflector second portion to said first reflector first portion and said second reflector first portion, respectively, permitting adjustment of the angles $\gamma_1$ and $\gamma_2$.

12. Apparatus as claimed in claim 9, further comprising mounts pivotally mounting said first reflector second portion and said second reflector second portion to said first reflector first portion and said second reflector first portion, respectively, permitting adjustment of the angular positions of angles $\gamma_1$ and $\gamma_2$.

13. Apparatus as claimed in claim 9, wherein $\beta_1=\beta_2$.

14. Apparatus as claimed in claim 13, wherein $\gamma_1=\gamma_2$.

15. Apparatus as claimed in claim 9, wherein $\gamma_1=\gamma_2$.

16. Apparatus as claimed in claim 1, wherein said third reflector extends from said trough first end at an angle $\delta_1>90°$, and said fourth reflector extends from said trough second end at an angle $\delta_2>90°$.

17. Apparatus as claimed in claim 16, further comprising mounts pivotally mounting said third and fourth reflectors to said trough first and second ends, respectively, permitting adjustment of the angle $\delta_1$ and $\delta_2$.

18. Apparatus as claimed in claim 16, wherein angle $\delta_1=\delta_2$.

19. Apparatus as claimed in claim 1, wherein said irradiation source is a discharge bulb.

20. Apparatus as claimed in claim 19, wherein said bulb is a tubular bulb.

21. Apparatus as claimed in claim 20, wherein said irradiation source is a light source.

22. Apparatus as claimed in claim 21, wherein said light source is a source of ultraviolet light.

23. Apparatus as claimed in claim 22, wherein said source of ultraviolet light is a microwave electrodeless discharge bulb.

24. Apparatus as claimed in claim 22, wherein said source of ultraviolet light is an arc discharge bulb.

25. Apparatus as claimed in claim 24, wherein said source of ultraviolet light is a fluorescent discharge bulb.

26. Apparatus as claimed in claim 1, wherein said translucent reflector is on the focal axis of said trough.

27. Apparatus as claimed in claim 1, further comprising a mount adjustably mounting said irradiation source on the major axis of said trough, permitting adjustment of the position of said irradiation source on the major axis of said trough.

28. A method of providing a substantially two-dimensionally uniform irradiation distribution on a planar target surface, said method comprising:

providing the structure of claim 5;

adjusting the angular positions of said translucent reflector second and third planar portions relative to said first planar portion; and activating said irradiation source to provide a substantially two-dimensionally uniform distribution of irradiation from said irradiation source onto the planar target surface.

29. A method of providing a substantially two-dimensionally uniform irradiation distribution on a planar target surface, said method comprising:

providing the structure of claim 10;

adjusting the angular positions of said first reflector first portion and said second reflector first portion relative to said trough; and activating said irradiation source to provide a substantially two-dimensionally uniform distribution of irradiation from said irradiation source onto the planar target surface.

30. A method of providing a substantially two-dimensionally uniform irradiation distribution on a planar target surface, said method comprising:

providing the structure of claim 11;

adjusting the angular positions of said first reflector first portion and said second reflector first portion relative to said trough;

adjusting the angular positions of said first reflector second portion and said second reflector second portion relative to said first reflector first portion and said second reflector first portion, respectively; and activating said irradiation source to provide a substantially two-dimensionally uniform distribution of irradiation from said irradiation source onto the planar target surface.

31. A method of providing a substantially two-dimensionally uniform irradiation distribution on a planar target surface, said method comprising:

providing the structure of claim 12;

adjusting the angular positions of said first reflector second portion and said second reflector second portion relative to said first reflector first portion and said second reflector first portion, respectively; and activating said irradiation source to provide a substantially two-dimensionally uniform distribution of irradiation from said irradiation source onto the planar target surface.

32. A method of providing a substantially two-dimensionally uniform irradiation distribution on a planar target surface, said method comprising:

providing the apparatus of claim 27;

adjusting the position of said irradiation source on the major axis of said trough; and activating said irradiation source to provide a two-dimensionally substantially uniform distribution of irradiation from said irradiation source onto the planar target surface.

* * * * *